US010909676B2

(12) United States Patent
Passerini et al.

(10) Patent No.: US 10,909,676 B2
(45) Date of Patent: Feb. 2, 2021

(54) METHOD AND SYSTEM FOR CLINICAL DECISION SUPPORT WITH LOCAL AND REMOTE ANALYTICS

(71) Applicant: Siemens Healthcare GmbH, Erlangen (DE)

(72) Inventors: Tiziano Passerini, Plainsboro, NJ (US); Lucian Mihai Itu, Brasov (RO); Dorin Comaniciu, Princeton Junction, NJ (US); Puneet Sharma, Monmouth Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 287 days.

(21) Appl. No.: 15/647,302

(22) Filed: Jul. 12, 2017

(65) Prior Publication Data

US 2019/0019286 A1 Jan. 17, 2019

(51) Int. Cl.
 *G06K 9/00* (2006.01)
 *G06T 7/00* (2017.01)
 (Continued)

(52) U.S. Cl.
 CPC .......... *G06T 7/0012* (2013.01); *A61B 5/0035* (2013.01); *A61B 5/02007* (2013.01);
 (Continued)

(58) Field of Classification Search
 CPC . G06T 2207/10016; G06T 2207/10056; G06T 2207/10148; G06T 2207/30024;
 (Continued)

(56) References Cited

U.S. PATENT DOCUMENTS

| 6,906,998 B1* | 6/2005 | Mujeeb | ................ H04L 49/552 370/218 |
| 8,457,121 B1* | 6/2013 | Sharma | ............... H04L 41/0663 370/389 |

(Continued)

FOREIGN PATENT DOCUMENTS

WO WO2016075331 5/2016

OTHER PUBLICATIONS

Extended European Search Report (EESR) dated Dec. 11, 2018 in corresponding European Patent Application No. 18183193.4.
(Continued)

*Primary Examiner* — Avinash Yentrapati

(57) ABSTRACT

A method and system for non-invasive medical image based assessment of coronary artery disease (CAD) for clinical decision support using on-site and off-site processing is disclosed. Medical image data of a patient is received. A processing strategy for assessing CAD of the patient using one of on-site processing, off-site processing, or joint on-site and off-site processing is automatically selected based on clinical requirements for a current clinical scenario. Non-invasive assessment of CAD of the patient is performed based on the medical image data of the patient using one of on-site processing, off-site-processing, or joint on-site and off-site processing according to the selected processing strategy. A final assessment of CAD of the patient is output based on the non-invasive assessment of CAD.

17 Claims, 6 Drawing Sheets

(51) Int. Cl.
*A61B 5/02* (2006.01)
*A61B 6/03* (2006.01)
*G06K 9/66* (2006.01)
*A61B 5/00* (2006.01)
*A61B 6/00* (2006.01)
*A61B 8/00* (2006.01)
*A61B 8/08* (2006.01)

(52) U.S. Cl.
CPC ............... *A61B 6/032* (2013.01); *G06K 9/66* (2013.01); *A61B 6/504* (2013.01); *A61B 6/563* (2013.01); *A61B 8/0891* (2013.01); *A61B 8/565* (2013.01); *G06K 2009/00932* (2013.01); *G06T 2207/10081* (2013.01); *G06T 2207/10088* (2013.01); *G06T 2207/10108* (2013.01); *G06T 2207/10132* (2013.01); *G06T 2207/30101* (2013.01); *G06T 2211/404* (2013.01)

(58) Field of Classification Search
CPC ......... G06T 2207/30048; G06T 7/0016; G06T 7/571
See application file for complete search history.

(56) References Cited

U.S. PATENT DOCUMENTS

| | | | | |
|---|---|---|---|---|
| 8,781,152 B2* | 7/2014 | Momeyer | ............. | G06K 9/228 382/100 |
| 9,349,178 B1* | 5/2016 | Itu | ............. | A61B 5/7267 |
| 9,538,925 B2* | 1/2017 | Sharma | ............. | G16H 50/30 |
| 9,595,089 B2 | 3/2017 | Itu et al. | | |
| 2003/0026470 A1* | 2/2003 | Kasai | ............. | G16H 15/00 382/132 |
| 2003/0095693 A1* | 5/2003 | Kaufman | ............. | G06T 5/002 382/128 |
| 2004/0022453 A1* | 2/2004 | Kusama | ............. | G06T 11/00 382/284 |
| 2004/0114714 A1* | 6/2004 | Minyard | ............. | A61B 5/7435 378/37 |
| 2004/0120557 A1* | 6/2004 | Sabol | ............. | G09B 23/28 382/128 |
| 2010/0040281 A1* | 2/2010 | Chen | ............. | G06N 3/0454 382/156 |
| 2011/0092825 A1* | 4/2011 | Gopinathan | ............. | G16H 40/67 600/483 |
| 2011/0206249 A1* | 8/2011 | Mathew | ............. | G16H 30/40 382/128 |
| 2011/0213889 A1* | 9/2011 | Krotz | ............. | G16H 30/20 709/228 |
| 2011/0224542 A1* | 9/2011 | Mittal | ............. | G06T 7/143 600/425 |
| 2012/0033876 A1* | 2/2012 | Momeyer | ............. | G06K 9/228 382/165 |
| 2012/0072190 A1* | 3/2012 | Sharma | ............. | G06T 7/0016 703/2 |
| 2013/0132054 A1* | 5/2013 | Sharma | ............. | G16B 5/00 703/9 |
| 2013/0246034 A1* | 9/2013 | Sharma | ............. | A61B 6/503 703/11 |
| 2014/0058715 A1* | 2/2014 | Sharma | ............. | A61B 6/032 703/11 |
| 2014/0119614 A1* | 5/2014 | Mochizuki | ............. | G06F 16/24 382/110 |
| 2015/0023602 A1* | 1/2015 | Wnuk | ............. | G06F 19/00 382/190 |
| 2015/0066538 A1* | 3/2015 | Dantsker | ............. | G16H 10/60 705/3 |
| 2015/0112182 A1* | 4/2015 | Sharma | ............. | A61B 5/7282 600/408 |
| 2015/0324962 A1* | 11/2015 | Itu | ............. | A61B 5/02007 382/130 |
| 2016/0106321 A1* | 4/2016 | Sharma | ............. | A61B 6/5217 600/407 |
| 2016/0148371 A1* | 5/2016 | Itu | ............. | A61B 6/5217 382/128 |
| 2017/0032097 A1* | 2/2017 | Itu | ............. | G16H 50/50 |
| 2018/0042565 A1* | 2/2018 | Wilson | ............. | A61B 6/5235 |
| 2018/0253531 A1* | 9/2018 | Sharma | ............. | A61B 6/503 |

OTHER PUBLICATIONS

Sharma, et al; A framework for personalization of coronary flow computations during rest and hyperemia. In: Engineering in Medicine and Biology Society (EMBC), 2012 Annual International Conference of the IEEE, 6665-6668, IEEE, 2012.

* cited by examiner

METHOD AND SYSTEM FOR CLINICAL DECISION SUPPORT WITH LOCAL AND REMOTE ANALYTICS

BACKGROUND OF THE INVENTION

The present invention relates to non-invasive medical image-based assessment of coronary artery disease, and more particularly, to clinical decision support for non-invasive local and remote computer based assessment of coronary artery disease.

Cardiovascular disease (CVD) is the leading cause of deaths worldwide. Among various CVDs, coronary artery disease (CAD) accounts for nearly fifty percent of those deaths. Local narrowing of a blood vessels, or stenosis, represents an important cause of cardiovascular diseases. Such stenoses typically develop gradually over time, and can develop in different parts of the arterial circulation, such as the coronary arteries, renal arteries, peripheral arteries, carotid artery, cerebral artery, etc. Such a local narrowing can also be the result of a congenital defect. One therapy widely used for treating arterial stenosis is stenting, i.e., the placement of a metal or polymer stent in the artery to open up the lumen, and hence facilitate the flow of blood. When dealing with coronary artery stenosis, the stenting therapy is referred to as percutaneous coronary intervention (PCI).

The current clinical practice for diagnosis and management of coronary stenosis involves the assessment of the diseased vessel either visually or by Quantitative Coronary Angiography (QCA). Such assessment provides the clinician with an anatomical overview of the stenosis segment and parent vessel, including the area reduction, lesion length, and minimal lumen diameter, but does not provide a functional assessment of the effect of the lesion on blood flow through the vessel. Measuring the fractional flow reserve (FFR) by inserting a pressure wire into the stenosed vessel has been shown to be a better option for guiding revascularization decisions, since the FFR is more effective in identifying ischemia causing lesions, as compared to invasive angiography. However, such invasive pressure wire based FFR measurements involve risks associated with the intervention necessary to insert the pressure wire into the vessel, and for a very narrow stenosis, the pressure wire may induce an additional pressure drop.

In recent years, various technologies have been developed for non-invasive, medical image-based assessment of human physiology and pathology. For example, various techniques utilize personalize physiological modeling for the non-invasive assessment of coronary artery disease. However, such techniques differ in several respects, including the type and quality of analyses performed and the processing time needed to perform the analyses.

BRIEF SUMMARY OF THE INVENTION

The present invention provides a method and system to perform non-invasive assessment of coronary artery disease (CAD) and to support clinical decisions regarding how to non-invasively assess CAD in various clinical scenarios. Embodiments of the present invention generate an optimized hybrid workflow, combining on-site and off-site processing for the non-invasive assessment of CAD, by automatically selecting a CAD assessment strategy for a patient that best fits the clinical problem at hand, and then performs non-invasive assessment of CAD for the patient using the optimized workflow.

In one embodiment of the present invention, medical image data of a patient is received. A processing strategy for assessing CAD of the patient using one of on-site processing, off-site processing, or joint on-site and off-site processing is automatically selected based on clinical requirements for a current clinical scenario. Non-invasive assessment of CAD of the patient is performed based on the medical image data of the patient using one of on-site processing, off-site-processing, or joint on-site and off-site processing according to the selected processing strategy. A final assessment of CAD of the patient is output based on the non-invasive assessment of CAD.

These and other advantages of the invention will be apparent to those of ordinary skill in the art by reference to the following detailed description and the accompanying drawings.

DETAILED DESCRIPTION

Figure 1:
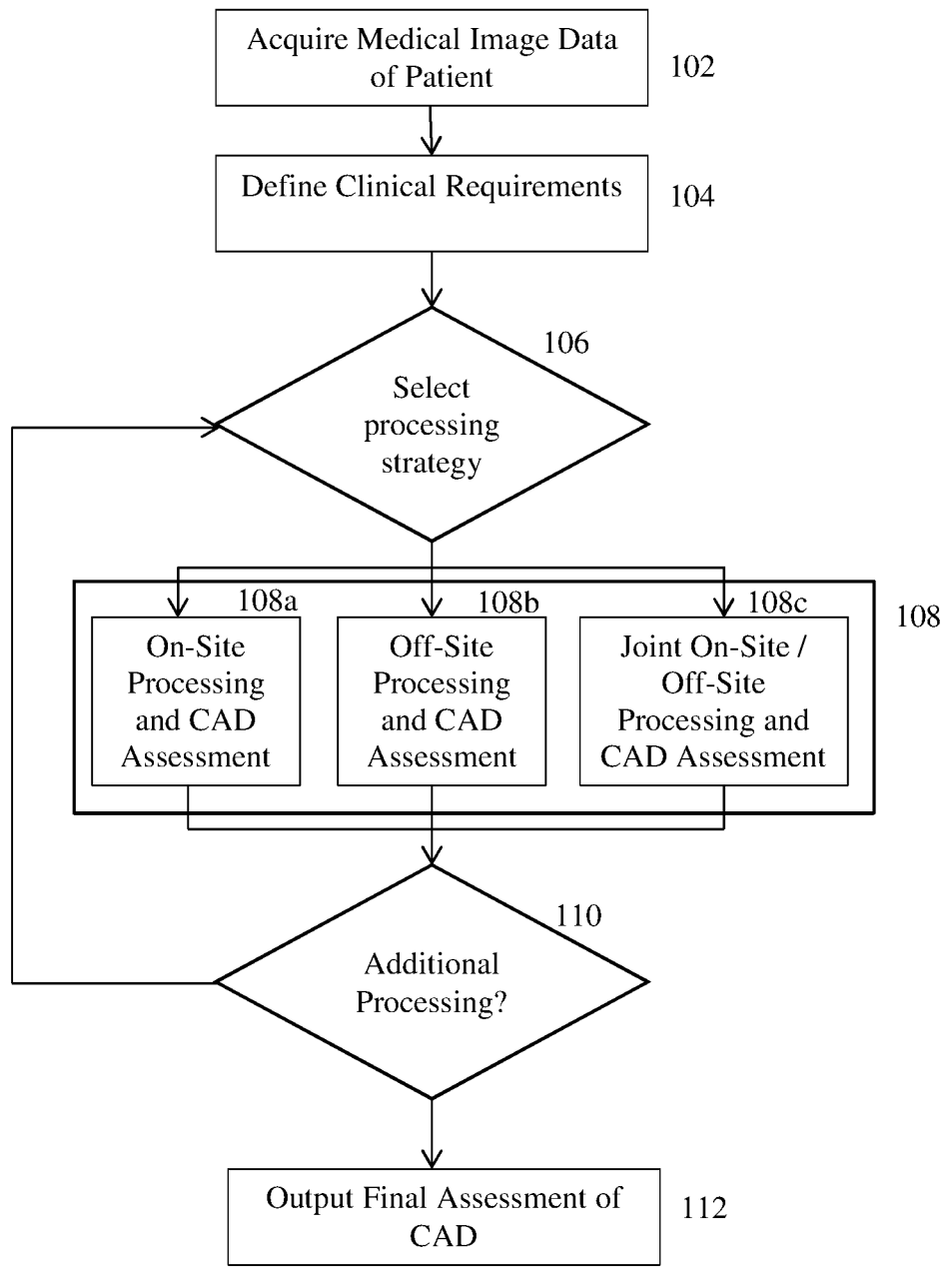
FIG. 1 illustrates a method for non-invasive assessment of coronary artery disease (CAD) of a patient according to an embodiment of the present invention.

The present invention relates to a method and system to perform non-invasive assessment of coronary artery disease (CAD) and to support clinical decisions regarding how to non-invasively assess CAD in various clinical scenarios. Embodiments of the present invention are described herein to give a visual understanding of the methods for medical image-based non-invasive assessment of CAD. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

A range of technologies have been developed for the non-invasive, image-based assessment of human physiology and pathology. They differ in several respects, including the type and quality of analyses performed, and the processing time needed. For example, various techniques have been developed that utilize personalized physiological modeling for the assessment of CAD. The overall workflow for personalized, image-based physiological modeling typically includes the analysis of medical images, extraction of geometric features from the medical images, and use of these features to determine a quantity of interest (e.g., FFR). Some approaches utilize computational modeling of a patient's blood flow to perform the non-invasive assessment of CAD. Typically, in such computational approaches, an anatomical model of the arterial tree is reconstructed based on the medical images after image segmentation, a computational fluid dynamics model is personalized to describe the patient-specific hemodynamics, and quantities of interest (e.g., FFR) are computed based on simulated blood flow and pressure values computed using the personalized computational fluid dynamics model. Alternative approaches utilize machine learning techniques to perform non-invasive assessment of CAD. In such machine-learning based approaches, geometric features are extracted directly from the images, and the geometric features are given as input to a trained predictor (e.g., a machine learning algorithm) to compute the quantities of interest. For example, a machine learning algorithm can be used to predict FFR from geometric features of the patient-specific coronary tree extracted from medical image data of a patient.

The computation of the quantities of interest for non-invasive assessment of CAD can be performed interactively on the same system that acquires or visualizes patient-specific medical images (local or on-site processing); or it can be performed on a different system and at a different time (remote or off-site processing). Different techniques for non-invasive assessment of CAD may be available using remote or off-site processing as compared to those available for local or on-site processing at a particular medical facility. For example, in a possible embodiment, the on-site processing may calculate quantities of interest using a machine-learning based approach and the off-site processing may compute quantities of interest using computational approach. Typically, on-site processing will produce results faster as compared to off-site processing, but off-site processing may provide more detailed or accurate results.

According to an embodiment of the present invention, different approaches involving on-site or off-site assessment of CAD, or a combination of the two, may be desirable to support the decision making process in different clinical scenarios. Embodiments of the present invention utilize the constraints of the clinical workflow in generating an optimal CAD assessment strategy. For example, embodiments of the present invention can take into account whether a current clinical scenario is an emergency or non-emergency situation when determining whether to utilize on-site or off-site non-invasive assessment of CAD. In an emergency situation, such as when a CT scan is performed for a patient in the emergency room (ER) an acute therapy decision has to be made in limited time, on-site non-invasive assessment of CAD (only based on CT images) can be a valuable solution due to shorter processing time; and off-site processing may not be a valid option due to time constraints. In non-emergency situations, off-site assessment of CAD can provide more detailed information or additional information that may not be available using on-site processing. A strategy that includes such off-site processing can be selected in this situation by utilizing a less strict requirement on the processing time. Examples of such scenarios include accessing a different computational model available off-site but not on-site, providing different analyses or options as compared to the on-site processing (e.g., plaque analysis may be only available off-site), running multiple computational models off-site and reporting their results in a combined way, or accessing an updated version of the computational model or of the training database that is only available off-site. In another example scenario, on-site assessment may not be available at the time when the medical images are acquired. This may be due for instance to limitations of the imaging workstation (incompatible hardware or software configuration), or unavailability of the workstation providing the on-site processing functionality. In this case, off-site processing can be offered as an alternative, to produce the same results as the on-site counterpart, or with the possibility of choosing different analyses or options.

FIG. 1 illustrates a method for non-invasive assessment of coronary artery disease (CAD) of a patient according to an embodiment of the present invention. The method of FIG. 1 generates an optimized strategy for non-invasive assessment of CAD using on-site processing, off-site processing, or joint on-site and off-site processing based on specific clinical requirements of the current clinical scenario, and utilizes the optimized strategy to provide a final assessment of CAD for the patient.

At step 102, medical image data of the patient is acquired. Medical imaging data from one or multiple imaging modalities can be acquired. For example, the medical imaging data can include, computed tomography (CT), Dyna CT, magnetic resonance (MR), Angiography, Ultrasound, Single Photon Emission computed Tomography (SPECT), and any other type of non-invasive medical imaging modality. The medical image data can be 2D, 3D, or 4D (3D+time) medical image data. The medical image data can be acquired using one or more image acquisition devices, such as a CT scanner, MR scanner, Angiography scanner, Ultrasound device, etc., or the medical image data may be received by loading previously stored medical image data for a patient.

In an advantageous embodiment, 3D coronary CT angiography (CTA) images are acquired on a CT scanner. The CTA images ensure that coronary vasculature, including the vessel(s) that contain the stenosis, is adequately imaged using a contrast agent that is injected into the patient. At this stage, the clinician may be provided with an option of identifying lesions (stenoses) of interest by interactively viewing them on the images. Alternatively, the stenoses may be automatically detected in the image data using an algorithm for automatic detection of coronary artery stenosis, such as the method for automatic detection of coronary artery stenosis described in United States Published Patent Application No. 2011/0224542, which is incorporated herein by reference. This step can also be performed during extraction of a patient-specific anatomical model that is extracted from the image data during the on-site or off-site processing. In addition to the medical image data, other non-invasive clinical measurements, such as the patient's heart rate and systolic and diastolic blood pressure may also be acquired.

At step 104, clinical requirements are defined for a current clinical scenario. The clinical requirements can include time requirements, such as a deadline by which an assessment of CAD is needed, cost requirements, fidelity/quality requirements, resources currently available on-site (e.g., the hardware and/or software configuration of a current workstation or the availability of other workstations with processing functionality needed for on-site processing), the type of imaging data and non-invasive clinical measurements available, a purpose/endpoint for the CAD assessment (e.g., general assessment/diagnosis, therapy planning, emergency situation, etc.) and/or other requirements that further define the current clinical scenario. One or more of such requirements can be input manually by a user. In an exemplary implementation, a graphical user interface can be displayed on a display/screen of a workstation (computer) that prompts a user to fill in the clinical requirements or information that can be used to define the clinical requirements. In another embodiment, the clinical requirements may include clinical indicators that are automatically extracted from the medical image data and/or the non-invasive clinical parameters. For example, calcium scoring can be automatically performed in the medical image data of the patient and used as clinical indicator for determining the processing strategy. In a possible implementation, the calcium scoring can be automatically performed using a trained machine learning based classifier. In an exemplary implementation, since different algorithms for non-invasive assessment of CAD have different accuracy for patients with high calcium scoring, the actual calcium score can be calculated and used as one of multiple clinical indicators upon which the selection of the processing strategy is based.

At step 106, a processing strategy is automatically selected for the current clinical scenario based on the clinical requirements. Based on the clinical requirements defined in step 104, an optimal strategy is selected of how to best use available on-site and/or off-site CAD assessment algorithms to provide an assessment of CAD in the current clinical scenario. Based on the clinical requirements, it is determined whether to perform on-site CAD assessment, off-site CAD assessment, or joint on-site/off-site CAD assessment. An intelligent artificial agent (i.e., a trained algorithm) selects or designs the processing strategy based on the clinical requirements and information about the available on-site and off-site CAD assessment algorithms.

In one embodiment, the strategy selection algorithm can be a machine learning based algorithm running on an on-site computer system. For example, such a machine learning based algorithm can be run directly on a computer system incorporated in the medical image scanner used to acquire the image data of the patient or on a picture archiving and communication system (PACS). The machine learning based intelligent artificial agent can analyze the complexity of the case by evaluating a clinical indicator, such as calcium scoring, in the image data of the patient, and then decide whether to send the image data off-site, process the image data on-site, or to select a joint on-sit and off-site processing strategy for assessing CAD for the patient. The machine learning based agent can be trained by retrospectively analyzing large databases of patient-specific medical data and the corresponding outcomes or clinical history of the patients in order to learning what kind of processing strategies were implemented to provide the clinicians with accurate information for the optimal care of the patient and what choices were not optimal (e.g., in terms of time or cost efficiency). In addition, additional training data can be generated using simulated clinical studies, from which the agent can learn the effect of different processing strategies with assessment of CAD, given various clinical scenarios and patient medical image data. Various machine learning techniques can be used to train the machine learning based intelligent artificial agent. In an advantageous embodiment, the intelligent artificial agent can be implemented using a deep reinforcement learning based algorithm (DRL) that has been trained offline to learn an optimal policy for selecting the non invasive CAD assessment strategy. Such an optimal policy can also be seen as an optimal trajectory that a user has to follow in order to reach the desired result (ground-truth). In our example presented above, the trajectory will be represented by the set of choices that a user chooses at each step of the proposed decision workflow (what kind of non-invasive CAD assessment to choose). One way to train a DRL algorithm is to use a training database that consists of training examples (i.e. trajectories) generated by one or more users who have performed the task of selection the CAD assessment strategy, given the clinical context. Another way would be to generate a training database "synthetically", i.e. by creating examples by using one or more image processing and computational modeling algorithm(s).

In another embodiment, the strategy selection algorithm can select the processing strategy using based on multi-objective optimization of a mathematical function describing different aspects of each data processing strategy, such as time-effectiveness, cost, accuracy, etc.

At step 108, non-invasive assessment of CAD for the patient is performed based on the medical image data of the patient according to the selected processing strategy for the current clinical scenario. The processing strategy selected at step 106 can be to perform on-site processing and CAD assessment (108*a*), off-site processing and CAD assessment (108*b*), or joint on-site and off-site processing and CAD assessment (108*c*). Accordingly, based on the processing strategy selected at step 106, step 108*a*, 108*b*, or 108*c* is performed.

At step 108*a*, on-site processing and CAD assessment is performed. In particular, on on-site CAD assessment algorithm is performed using one or more local computers or processors in an on-site computer system to perform the processing operations thereof. In an advantageous embodiment, the on-site processing and CAD assessment can be performed using a machine learning based algorithm. For example, in a possible implementation, an on-site machine learning algorithm can be used to predict FFR, pressure drop, or other hemodynamic indices (e.g., coronary flow reserve (CFR), instantaneous wave-free ratio (IFR), hyperemic stress reserve (HSR), basal stenosis resistance (BSR), index of microcirculatory resistance (IMR), etc.) from geometric features of the patient's coronary arteries extracted from medical image data of the patient. In this case, the on-site machine-learning based method for CAD assessment can be performed by extracting geometric features from a patient-specific anatomical model of the coronary arteries extracted from the medical image data or directly from the medical image data, inputting the extracted geometric features to a trained machine learning-based model, and computing the hemodynamic quantities of interest using the trained machine learning-based model. The machine-learning based model can be trained using any type of machine learning algorithm. In another possible implementation, a deep learning architecture can be used to predict FFR or other hemodynamic quantities of interest directly from the medical image data. For example, the CAD assessment may be performed by detecting image patches corresponding to a stenosis of interest and the coronary artery tree in the medical image data of the patient, inputting the image patches directly to a trained deep neural network regressor, and computing the hemodynamic quantities of interest using the trained deep neural network regressor applied directly to the image patches. Various machine-learning based algorithms for non-invasive assessment of CAD are described in greater detail in U.S. Pat. No. 9,538,925, issued Jan. 10, 2017, entitled "Method and System for Machine Learning Based Assessment of Fractional Flow Reserve", U.S. Pat. No. 9,349,178, issued May 24, 2016, entitled "Synthetic Data-Driven Hemodynamic Determination in Medical Imaging", International Patent Publication No. WO 2016/075331 A2, filed Nov. 16, 2015, entitled "Method and System for Purely Geometric Machine Learning Based Fractional Flow Reserve", and U.S. Publication No. 2015/0112182, filed Oct. 16, 2014 entitled "Method and System for Machine Learning Based Assessment of Fractional Flow Reserve", the disclosures of which are incorporated herein in their entirety by reference. In another possible embodiment, the on-site processing and CAD assessment can be performed using a computational algorithm in which blood flow in the coronary arteries is simulated using a CFD model and the hemodynamic quantities of interest are calculated based on the simulated blood flow. Additional details regarding CFD-based algorithms for CAD assessment are described below.

At step 108b, off-site processing and assessment of CAD is performed. In this case, the medical image data and clinical measurements of the patient are transmitted to an off-site computer system, such as a remote server or cloud computing system, and the off-site computer system performs the processing operations of a CAD assessment algorithm and returns the resulting hemodynamic quantities of interest to the on-site system. In a possible implementation, multiple off-site CAD assessment algorithms may be available and the processing strategy selected in step 106 may include selection of a specific off-site CAD assessment algorithm from the available off-site CAD assessment algorithms. In this case, the on-site computer system can transmit a request for the selected specific off-site CAD assessment algorithm to be performed.

In an advantageous embodiment, the off-site processing and CAD assessment may be performed using a computational modeling (e.g., CFD-based) algorithm. For example, computational CAD assessment can be performed by segmenting the coronary arteries in the medical image data of the patient to generate a patient-specific anatomical model of the coronary arterial tree, personalizing a CFD model of coronary arterial circulation based on the patient-specific anatomical model and clinical measurements of the patient to model the patient-specific hemodynamics, simulating blood flow and pressure in the coronary arteries using the personalized CFD model, and computing hemodynamic quantities of interest (e.g., FFR, pressure drop, coronary flow reserve (CFR), instantaneous wave-free ratio (IFR), hyperemic stress reserve (HSR), basal stenosis resistance (BSR), index of microcirculatory resistance (IMR), etc.) based on the simulated blood flow and pressure values. Various CFD models (e.g., full scale 3D CFD model, multi-scale CFD model, reduced order 1D model, etc.) can be used to perform the CFD blood flow and pressure simulations, and various techniques can be used to compute patient-specific boundary conditions to personalize the CFD model. Various computational (e.g., CFD-based) techniques for CAD assessment are described in greater detail U.S. Publication No. 2014/0058715, filed Nov. 4, 2013, entitled "Method and System for Non-Invasive Functional Assessment of Coronary Artery Stenosis", U.S. Publication No. 2013/0246034, filed Mar. 11, 2013, entitled "Method and System for Non-Invasive Functional Assessment of Coronary Artery Stenosis", U.S. Publication No. 2013/0132054, filed Nov. 9, 2012, entitled "Method and System for Multi-Scale Anatomical and Functional Modeling of Coronary Circulation", U.S. Publication No. 2012/0072190, filed Sep. 7, 2011, entitled "Method and System for Non-Invasive Assessment of Coronary Artery Disease", and U.S. Pat. No. 9,595,089, issued Mar. 14, 2017, entitled "Method and System for Non-Invasive Computation of Hemodynamic Indices for Coronary Artery Stenosis", the disclosures of which are incorporated herein in their entirety by reference. In another possible embodiment, the off-site processing and CAD assessment can be performed using a machine learning-based algorithm.

In an advantageous embodiment, the on-site processing and CAD assessment (108a) is performed using a machine learning based algorithm and the off-site processing and CAD assessment is performed using a computational (e.g., CFD-based) algorithm, but the present invention is not limited thereto and the on-site and off-site CAD assessment algorithms can be each implemented using a computational algorithm or a machine learning-based algorithm. In a possible embodiment, the on-site processing and CAD assessment (108a) can be performed using a first machine learning-based algorithm and the off-site processing and CAD assessment (108b) can be performed using a second machine learning-based algorithm that uses a more computationally intensive machine learning model than the first machine learning-based algorithm. For example, the on-site algorithm can use a machine learning model that inputs geometric features extracted from the medical image data and the off-site algorithm can use a deep learning architecture that directly inputs the medical image data. In another possible embodiment, the on-site processing and CAD assessment (108a) can be performed using a computational approach with a reduced-order CFD model and the off-site processing and CAD assessment (108b) can be performed using a computational approach with a multi-scale or full scale 3D CFD model.

Figure 2:
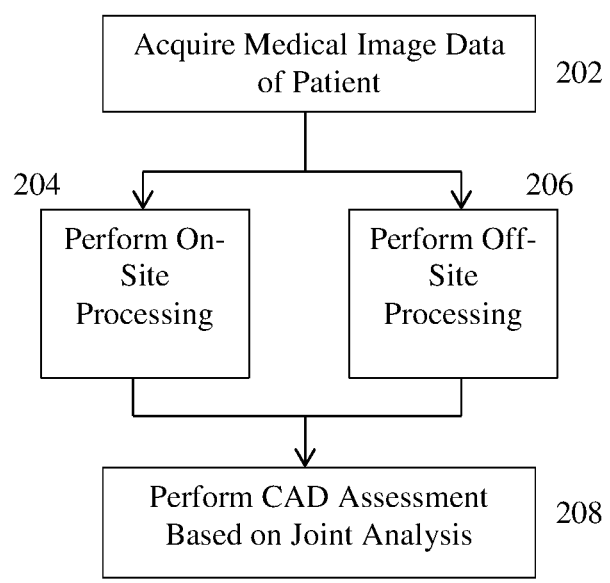
FIG. 2 illustrates a method for non-invasive assessment of CAD using joint on-site and off-site processing according to an embodiment of the present invention.

At step 108c, joint on-site and off-site processing and CAD assessment is performed according to the processing strategy selected at step 106. FIG. 2 illustrates a method for non-invasive assessment of CAD using joint on-site and off-site processing according to an embodiment of the present invention. Referring to FIG. 2, at step 202 medical image data of the patient is acquired. In addition to the medical image data, other non-invasive clinical measurements, such as the patient's heart rate and systolic and diastolic blood pressure may also be acquired. This step is similar to step 102 of FIG. 1. At step 204, on-site processing is performed. At step 206, off-site processing is performed. Steps 204 and 206 may be performed in parallel (e.g., simultaneously) or sequentially in any order based on the selected processing strategy. At step 208, CAD assessment is performed based on joint analysis of the on-site and off-site processing results. Step 208 can be performed by the on-site computer system or by the off-site computer system.

In one embodiment, the selected processing strategy for the joint on-site and off-site processing can be to perform both an on-site CAD assessment algorithm and a separate off-site CAD assessment algorithm. In this case, at step 204, the on-site computer system performs the on-site CAD assessment algorithm and generates first hemodynamic quantities or interest. The on-site CAD assessment algorithm can be either a machine-learning based algorithm or a computational algorithm, as described above. At step 204, the off-site computer system performs the off-site CAD assessment algorithm and generates second hemodynamic quantities of interest. For example, the medical image data of the patient and clinical measurements of the patient can be transmitted to the off-site computer system, along with a request for the off-site CAD assessment algorithm to be performed, the off-site computer system performs the requested off-site CAD assessment algorithm, and the resulting second hemodynamic quantities of interest are returned to the on-site computer system. At step 208, the CAD assessment is performed based on a joint analysis of the first and second hemodynamic quantities of interest. In a possible implementation, it can be determined if the first and second hemodynamic quantities of interest result in a consistent or inconsistent assessment of CAD. In particular, the first and second hemodynamic quantities (e.g., FFR) can each be compared to a predetermined threshold value for determining the severity of CAD. If both the first and second hemodynamic quantities of interest are above the threshold value or both the first and second hemodynamic quantiles of interest are below the threshold value, the on-site CAD assessment and off-site CAD assessment are consistent and can be used for a final assessment of the patient's CAD. If one of the first and second hemodynamic quantities of interest is above the threshold value and the other is below the threshold value, the on-site CAD assessment and the off-site CAD assessment are inconsistent, and more information or processing may be needed to determine the final assessment of the patient's CAD. In another possible implementation, the first and second hemodynamic quantities of interest are combined, for example by calculating an average or weighted average (e.g., with a relative weighting of the first and second hemodynamic quantities of interest either predetermined or defined in the processing strategy) of the first and second hemodynamic quantities of interest. The combined value can be compared to the threshold value to assess the severity of the patient's CAD. The combined value can also be output to provide the final assessment of CAD if no further processing is needed.

In another embodiment, the selected processing strategy for the joint on-site and off-site processing can be to use joint on-site and off-site processing to perform different operations of a CAD assessment algorithm. In this case, the on-site processing of step 204 is used to perform one or more operations of a CAD assessment algorithm and the off-site processing of step 206 is used to perform one or more operations of the CAD assessment algorithm. For example, in the case of a machine learning-based CAD assessment algorithm, various operations such as pre-processing the medical image data, extracting the anatomical model and/or the geometric features from the medical image data, and computing the hemodynamic quantities of interest using a training machine learning model, can be performed by the on-site processing or the off-site processing in any combination, as determined by the selected processing strategy. Similarly, in the case of a computational CAD assessment algorithm various operations, such as pre-processing the medical image data, extracting the anatomical model, personalizing the CFD model, performing the blood flow and pressure simulations, and computing the hemodynamic quantities of interest, can be performed by the on-site processing or the off-site processing in any combination, as determined by the selected processing strategy. At step 208, the operations performed using the on-site processing and the operations performed using the off-site processing are combined to generate the CAD assessment (e.g., to compute the hemodynamic quantities of interest. This step can be performed as part of the on-site or off-site processing.

Returning to FIG. 1, at step 110, it is determined whether additional processing is required for the non-invasive assessment of CAD for the patient. The hemodynamic quantities of interest can be compared to one or more threshold values to determine if a conclusive assessment of the patient's CAD has been achieved using the CAD assessment algorithm(s) performed using the current processing strategy. For example, a hemodynamic quantity of interest (e.g., FFR) can be compared to a predetermined threshold value used to assess the severity of CAD. If the hemodynamic quantity of interest is in a gray zone corresponding to a certain range of values above and below the threshold value, the current CAD assessment can be considered inconclusive and it can be determined that more processing is needed. If the hemodynamic quantity of interest is not within the gray zone, it can be determined that the current CAD assessment is concluded and no further processing is needed. In another exemplary implementation, multiple different quantities of interest computed using CAD assessment algorithm or quantities of interest computed using multiple different CAD assessment algorithms (e.g., on-site and off-site or multiple off-site) can be compared to threshold values in order to determine whether the assessments based on the various quantities of interest are consistent or inconsistent. If the assessments are inconsistent, it can be determined that additional processing is needed, whereas if the assessments are consistent, it can be determined that no further processing is needed.

When it is determined at step 110 that additional processing is needed, the method returns to step 106 and an updated processing strategy is selected. In particular, it is then determined what additional processing (on-site, off-site, or joint onsite and off-site) is needed. For example, an on-site or off-site CAD assessment algorithm previously not selected may be selected at this point or a new joint on-site/off-site processing strategy can be selected to improve the previous CAD assessment results. In a possible embodiment, it can be determined that additional physiological measurements of the patient, such as invasive physiological measurements, are needed in order to improve the CAD assessment results. In this case, a CAD assessment algorithm (on-site, off-site, or joint) that enhances the previous CAD assessment results based on newly received physiological measurements can be utilized, as described in U.S. Publication No. 2017/0032097, filed Jul. 27, 2016, entitled "Method and System for Enhancing Medical Image-Based Blood Flow Computations Using Physiological Measurements", the disclosure of which is incorporated herein in its entirety by reference. When it is determined that no additional processing is necessary, the method proceeds to step 112.

At step 112, a final assessment of CAD for the patient is output. The final assessment of CAD for the patient can include locations of stenoses and other types of CAD, as well as corresponding hemodynamic quantities of interest computed for each of the locations. The final assessment of CAD can also include a qualitative description of the severity of the CAD, which can be automatically assigned based on the hemodynamic quantities of interest. The final assessment of CAD can be output by displaying the final assessment of CAD on a display device, as well as storing the final assessment of CAD, for example in a PACS. In an exemplary implementation, the final assessment of CAD can be output by displaying a visualization of a patient-specific anatomical model of the coronary arterial tree extracted from the medical images, overlaid with visualizations of the stenoses or other CAD locations and values of corresponding hemodynamic quantities of interest. The visualization of the patient's coronary arteries can be color-coded to indicate severity of the CAD as various locations.

Figure 3:
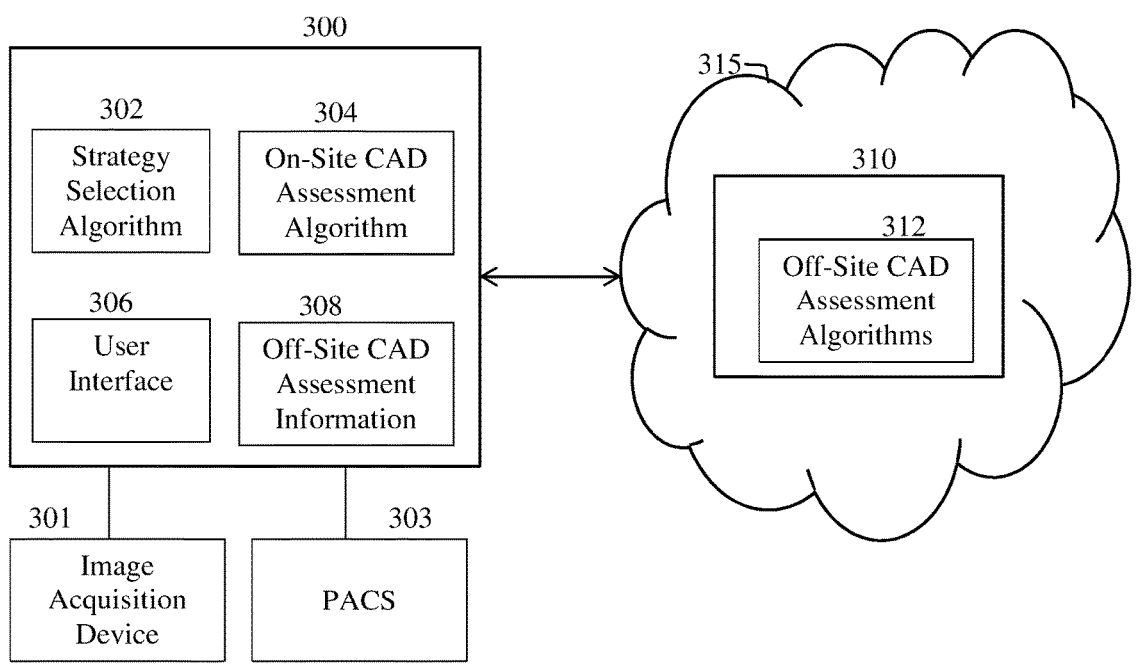
FIG. 3 illustrates a system for non-invasive assessment CAD of patients using on-site and off-site processing according to an embodiment of the present invention.

FIG. 3 illustrates a system for non-invasive assessment of coronary artery disease (CAD) of patients using on-site and off-site processing according to an embodiment of the present invention. As shown in FIG. 3, a local computer device 300 includes a strategy selection algorithm 302, an on-site CAD assessment algorithm 304, a user interface 306, and off-site CAD assessment information 308. The local computer device 301 communicates with one or more image acquisition device 301 and a picture archiving and communication system (PACS) 303. The local computer device 300 can be implemented using any type of computer device and includes computer processors, memory units, storage devices, computer software, and other computer components. In possible embodiments, the local computer device 300 can be implemented as a single device with the image acquisition device 301, as part of the PACS 303, or as a separate device that communicates wirelessly with the image acquisition device 301 and/or the PACS 303. In a possible embodiment, the local computer device can be a mobile device, such as a smart phone or tablet.

The image acquisition device 301 can be any type of medical image acquisition device, such as a CT scanner, MR scanner, C-arm image acquisition device, ultrasound device, etc. Medical images of a patient can be acquired using the image acquisition device 301, and the medical images can be sent to the local computer device 300 and/or stored in the PACS 303. The PACS 303 stores medical images of various modalities for various patients in a digital format. For example, the PACS 303 can use the Digital Imaging and Communications in Medicine (DICOM) format for storage and transfer of medical images. The local computer 300 can retrieve medical images stored in the PACS 303.

The local computer device 300 includes at least one on-site CAD assessment algorithm 304 and off-site CAD assessment information 308. The on-site CAD assessment algorithm 304 includes computer program instructions that define a computer-based method for non-invasive assessment of CAD. Such computer program instructions can be stored in the storage of the local computer device 300 and can be loaded into the memory of the local computer device 300 and executed by a processor of the local computer device 300 in order for the local computer device 300 to perform the on-site CAD assessment algorithm 304. For example, the on-site CAD algorithm 304 can be a machine-learning based method for non-invasive assessment of CAD or a method for non-invasive assessment of CAD using a computational fluid dynamics (CFD) model. In a possible implementation, multiple on-site CAD assessment algorithms 302 can be stored on the local computer device 300. The on-site CAD assessment algorithm 304 can also include individual algorithms for performing individual steps of one or more CAD assessment algorithms. In particular, computer program instructions defining such individual algorithms can be stored on the storage of the local computer device 300 and independently loaded into the memory and executed by the processor of the local computer device 300 in order for the local computer device to implement individual steps of a CAD assessment algorithm using on-site processing in a case in which the joint on-site and off-site processing is used to perform CAD assessment.

The on-site CAD assessment algorithm 304 may include one or more machine-learning based CAD assessment algorithm, such as the machine-learning based methods described in U.S. Pat. No. 9,538,925, issued Jan. 10, 2017, entitled "Method and System for Machine Learning Based Assessment of Fractional Flow Reserve", U.S. Pat. No. 9,349,178, issued May 24, 2016, entitled "Synthetic Data-Driven Hemodynamic Determination in Medical Imaging", International Patent Publication No. WO 2016/075331 A2, filed Nov. 16, 2015, entitled "Method and System for Purely Geometric Machine Learning Based Fractional Flow Reserve", and U.S. Publication No. 2015/0112182, filed Oct. 16, 2014 entitled "Method and System for Machine Learning Based Assessment of Fractional Flow Reserve", the disclosures of which are incorporated herein in their entirety by reference. The on-site CAD assessment algorithm 304 may include one or more computational CAD assessment algorithm, such as the computational methods described in U.S. Publication No. 2014/0058715, filed Nov. 4, 2013, entitled "Method and System for Non-Invasive Functional Assessment of Coronary Artery Stenosis", U.S. Publication No. 2013/0246034, filed Mar. 11, 2013, entitled "Method and System for Non-Invasive Functional Assessment of Coronary Artery Stenosis", U.S. Publication No. 2013/0132054, filed Nov. 9, 2012, entitled "Method and System for Multi-Scale Anatomical and Functional Modeling of Coronary Circulation", U.S. Publication No. 2012/0072190, filed Sep. 7, 2011, entitled "Method and System for Non-Invasive Assessment of Coronary Artery Disease", and U.S. Pat. No. 9,595,089, issued Mar. 14, 2017, entitled "Method and System for Non-Invasive Computation of Hemodynamic Indices for Coronary Artery Stenosis", the disclosures of which are incorporated herein in their entirety by reference.

The off-site CAD assessment information 308 includes information describing various off-site CAD assessment algorithms 312 that are available. For example, the off-site CAD assessment information 308 can include, for each of the available off-site CAD assessment algorithms 312, information such as processing time, cost, quantity/quantities of interest calculated (e.g., pressure drop, blood velocity, fractional flow reserve (FFR), etc.) fidelity/quality of quantities of interest, type of imaging data and/or non-invasive clinical measurements required, and any other type of information (e.g., technical information on network connection, such as network latency, uptime/downtime, etc.) that can be used as a basis for selecting the processing strategy by the strategy selection algorithm 302. The off-site CAD assessment information 308 can also include information regarding off-site processing algorithms available for individual steps of one or more CAD assessment algorithms, such as off-site algorithms for pre-processing medical image data, off-site algorithms for extracting geometric features and/or an anatomical model from medical image data, off-site CFD models available for performing blood flow simulations for CAD assessment, and off-site machine learning-based models available for CAD assessment.

The local computer device 300 communicates with one or more remote server 310 via a data network 315, such as the Internet. For example, the remote server 310 may be a server of a cloud-based computing system that can perform off-site non-invasive assessment of CAD and/or particular processing tasks related to non-invasive assessment of CAD. Various off-site CAD assessment algorithms 312 are stored on the remote server 310 or on another computer or storage device in the cloud based computing network. For example, the off-site CAD assessment algorithms 312 may include one or more methods for non-invasive assessment of CAD using CFD modeling and/or one or more machine-learning based methods for non-invasive assessment of CAD.

Typically, the on-site CAD assessment algorithm 304 will produce results faster as compared to the off-site CAD assessment algorithms 312, but off-site CAD assessment algorithms 312 may produce more detailed or accurate results. The on-site CAD assessment algorithm 304 typically will require less computing resources to perform as compared to the off-site CAD assessment algorithms 312. The off-site CAD assessment algorithms 312 may utilize different techniques as compared to the on-site CAD assessment algorithm 304. For example, in a possible embodiment, the on-site CAD assessment algorithm 304 may calculate quantities of interest (e.g., FFR, pressure drop, etc.) using a machine-learning based approach and the off-site CAD assessment algorithms 312 may compute quantities of interest using computational (e.g., CFD-based) approaches. Alternatively, the on-site CAD assessment algorithm 304 and the off-site CAD assessment algorithms 312 may utilize similar types of techniques, but the on-site CAD assessment algorithm 304 may be less computationally intensive than the off-site CAD assessment algorithms 312. For example, in a possible embodiment, the on-site CAD assessment algorithm 304 can include a CFD-based CAD assessment method that utilizes a reduced order CFD model of coronary blood flow and/or is tailored to compute a small set of physical quantities (e.g., average cross-sectional pressure, flow rate, FFR), while the off-site CAD assessment algorithms 312 can include CFD-based CAD assessment methods that utilize full-scale 3D or multi-scale CFD models and/or are tailored to provide a richer description of the blood flow physics (e.g., blood velocity, pressure, shear rate, wall shear stress, etc.). In another possible embodiment, the on-site CAD assessment algorithm 304 can include a machine learning based CAD assessment method that uses a first trained machine-learning based mapping, and the off-site CAD assessment algorithms 312 can include a machine learning based CAD assessment method that uses a second trained machine learning based mapping that is more computationally intensive that the first trained machine learning based mapping. For example, the second trained machine learning based mapping may generate a greater number of quantities of interest, may utilize a greater number of inputs to generate a quantity of interest, or in the case of deep learning, the second trained machine learning based mapping may have a greater number of hidden layers than the first trained machine learning based mapping. It is also possible, that different machine learning training techniques are used to train the machine learning based mappings used in the on-site CAD assessment algorithm 304 and the off-site CAD assessment algorithms 312.

The off-site CAD assessment algorithms 312 may include one or more computational CAD assessment algorithms, such as the computational CAD assessment algorithms described in U.S. Publication No. 2014/0058715, filed Nov. 4, 2013, entitled "Method and System for Non-Invasive Functional Assessment of Coronary Artery Stenosis", U.S. Publication No. 2013/0246034, filed Mar. 11, 2013, entitled "Method and System for Non-Invasive Functional Assessment of Coronary Artery Stenosis", U.S. Publication No. 2013/0132054, filed Nov. 9, 2012, entitled "Method and System for Multi-Scale Anatomical and Functional Modeling of Coronary Circulation", U.S. Publication No. 2012/0072190, filed Sep. 7, 2011, entitled "Method and System for Non-Invasive Assessment of Coronary Artery Disease", and U.S. Pat. No. 9,595,089, issued Mar. 14, 2017, entitled "Method and System for Non-Invasive Computation of Hemodynamic Indices for Coronary Artery Stenosis", the disclosures of which are incorporated herein in their entirety by reference. The off-site CAD assessment algorithms 312 may also include one or more machine learning-based CAD assessment algorithms, such as the machine learning-based CAD assessment algorithms described in U.S. Pat. No. 9,538,925, issued Jan. 10, 2017, entitled "Method and System for Machine Learning Based Assessment of Fractional Flow Reserve", U.S. Pat. No. 9,349,178, issued May 24, 2016, entitled "Synthetic Data-Driven Hemodynamic Determination in Medical Imaging", International Patent Publication No. WO 2016/075331 A2, filed Nov. 16, 2015, entitled "Method and System for Purely Geometric Machine Learning Based Fractional Flow Reserve", and U.S. Publication No. 2015/0112182, filed Oct. 16, 2014 entitled "Method and System for Machine Learning Based Assessment of Fractional Flow Reserve", the disclosures of which are incorporated herein in their entirety by reference.

The local computer device 300 includes a user interface 306. The user interface 306 can be a graphical user interface displayed on a display/screen of the local computer device 300. In an advantageous embodiment, the graphical user interface can prompt a user to fill in the clinical requirements for the current clinical scenario or information that can be used to define the clinical requirements. For example, the user can be prompted to enter clinical requirements including time requirements, such as a deadline by which an assessment of CAD is needed, cost requirements, fidelity/quality requirements, resources currently available on-site (e.g., the hardware and/or software configuration of a current workstation or the availability of other workstations with processing functionality needed for on-site processing), the type of imaging data and non-invasive clinical measurements available, a purpose for the CAD assessment (e.g., general assessment/diagnosis, therapy planning, emergency situation, etc.) and/or other requirements that further define the current clinical scenario. In addition the user interface 306 can display the final CAD assessment for the patient and various hemodynamic quantities of interest computed using the on-site and/or off-site CAD assessment algorithms 304 and 312.

The strategy selection algorithm 302 includes computer program instructions defining an intelligent artificial agent to select an optimal processing strategy based on the clinical requirements associate with the current clinical scenario. The strategy selection algorithm 302 automatically determines how to best use available on-site and/or off-site CAD assessment algorithms 304 and 312 to provide an assessment of CAD in the current clinical scenario. Based on the clinical requirements, the on-site CAD algorithm 304 and the off-site CAD assessment information 308, the strategy selection algorithm 302 determines whether to perform on-site CAD assessment, off-site CAD assessment, or joint on-site/off-site CAD assessment.

In one embodiment, the strategy selection algorithm 302 can be a machine learning based algorithm running on the local computer system 300. The machine learning based intelligent artificial agent can analyze the complexity of the case by evaluating a clinical indicator, such as calcium scoring, in the image data of the patient, and then decide whether to send the image data off-site, process the image data on-site, or to select a joint on-site and off-site processing strategy for assessing CAD for the patient. The machine learning based agent can be trained by retrospectively analyzing large databases of patient-specific medical data and the corresponding outcomes or clinical history of the patients in order to learning what kind of processing strategies were implemented to provide the clinicians with accurate information for the optimal care of the patient and what choices were not optimal (e.g., in terms of time or cost efficiency). In addition, additional training data can be generated using simulated clinical studies, from which the agent can learn the effect of different processing strategies with assessment of CAD, given various clinical scenarios and patient medical image data. Various machine learning techniques can be used to train the machine learning based intelligent artificial agent. In an advantageous embodiment, the intelligent artificial agent can be implemented using a deep reinforcement learning based algorithm (DRL) that has been trained offline to learn an optimal policy for selecting the non invasive CAD assessment strategy. Such an optimal policy can also be seen as an optimal trajectory that a user has to follow in order to reach the desired result (ground-truth). In our example presented above, the trajectory will be represented by the set of choices that a user chooses at each step of the proposed decision workflow (what kind of non-invasive CAD assessment to choose). One way to train a DRL algorithm is to use a training database that consists of training examples (i.e. trajectories) generated by one or more users who have performed the task of selection the CAD assessment strategy, given the clinical context. Another way would be to generate a training database "synthetically", i.e. by creating examples by using one or more image processing and computational modeling algorithm(s).

In another embodiment, the strategy selection algorithm 302 can select the processing strategy using based on multi-objective optimization of a mathematical function describing different aspects of each data processing strategy, such as time-effectiveness, cost, accuracy, etc.

The strategy selection algorithm 302 automatically selects on-site processing using the on-site CAD assessment algorithm 304, off-site processing using one or more of the available off-site CAD assessment algorithms 312, or joint on-site and off-site processing. In one embodiment, the joint on-site and off-site processing strategy selected by the strategy selection algorithm 302 can be to separately perform both the on-site CAD assessment algorithm 304 and one of the off-site CAD assessment algorithms 312, and then combine the results. In another embodiment, a CAD assessment algorithm can be performed using joint on-site and off-site processing, in which a mixture of on and off-site processing algorithms are used to perform individual steps of the CAD assessment algorithms. Various examples of processing strategies using such joint on-site and off-site processing are described below.

Evaluating what processing (on-site/off-site/joint) to perform can be based on different criteria depending on the clinical scenario or application. These criteria can include cost (the system favors the most cost-effective solution), time (the system favors the most time-effective solution), and availability of resources (the system excludes unavailable solutions). As an example of such criteria, based on the clinical question at hand, in emergency situations, a fast (on-site) answer to the clinical question may be selected over slower (off-site) processing, even in the case in which the less time-effective off-site processing leads to more accurate CAD assessment. In another example, to rule-in or rule-out clinical scenarios, high fidelity (off-site) processing may be required and low fidelity (on-site) processing may be selected because of time and cost effectiveness.

In another exemplary embodiment, the selection of on-site, off-site, or joint on and off-site processing may be based on the computational model available on-site or off-site. As described above, on-site and off-site processing can be performed with different computational modeling technologies, or with different implementations or parameterization of the same methodology. This leads to on-site and off-site processing pipelines potentially producing different analyses. In terms of fidelity, different computational models can represent the same quantity of interest (e.g., pressure drop, blood velocity, etc.) with different degrees of fidelity (e.g., spatially or temporally averaged, as opposed to time-space dependent variables. In terms of number of types of computed quantities, some computational models can be tailored to the computation of a small set of physical quantities (e.g., average cross-sectional pressure, flow rate, FFR), while different computational models can be employed to provide a richer description of the blood flow physics (e.g., blood velocity, shear rate, wall shear stress). Typically, longer processing times are required to run models with higher fidelity, which makes them suitable for execution off-site; while shorter processing times are typically required for lower fidelity models that can be run on-site. Similarly, models providing more detailed quantities or a larger set of quantities typically require longer processing time and are more conveniently executed off-site.

Figure 4:
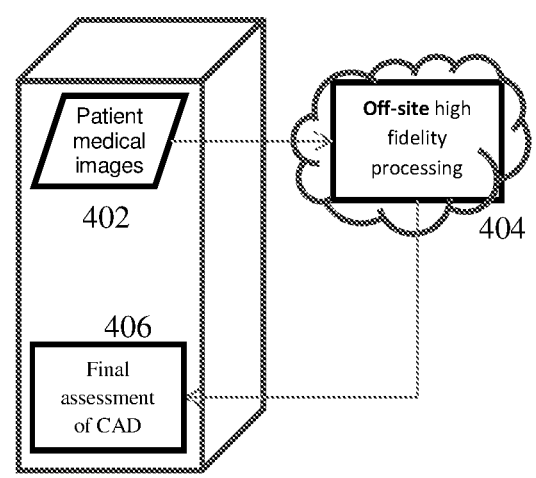
FIG. 4 illustrates an exemplary processing strategy in which off-site high fidelity processing is performed.

FIG. 4 illustrates an exemplary processing strategy in which off-site high fidelity processing is performed. The processing strategy of FIG. 4 can be selected based on the availability of an off-site CAD assessment algorithm using a high-fidelity computational model. As shown in FIG. 4, patient medical images 402 are acquired on-site and transmitted to a remote system where off-site high fidelity processing 404 is performed. The high fidelity processing 404 simulates hemodynamic quantities (e.g., pressure drop, blood velocity, etc.) with a high degree of fidelity (e.g., time and space dependent). The hemodynamic quantities simulated using the high-fidelity processing 404 are returned to the local computer system, which performs the final assessment of CAD 406 based on these quantities.

Figure 5:
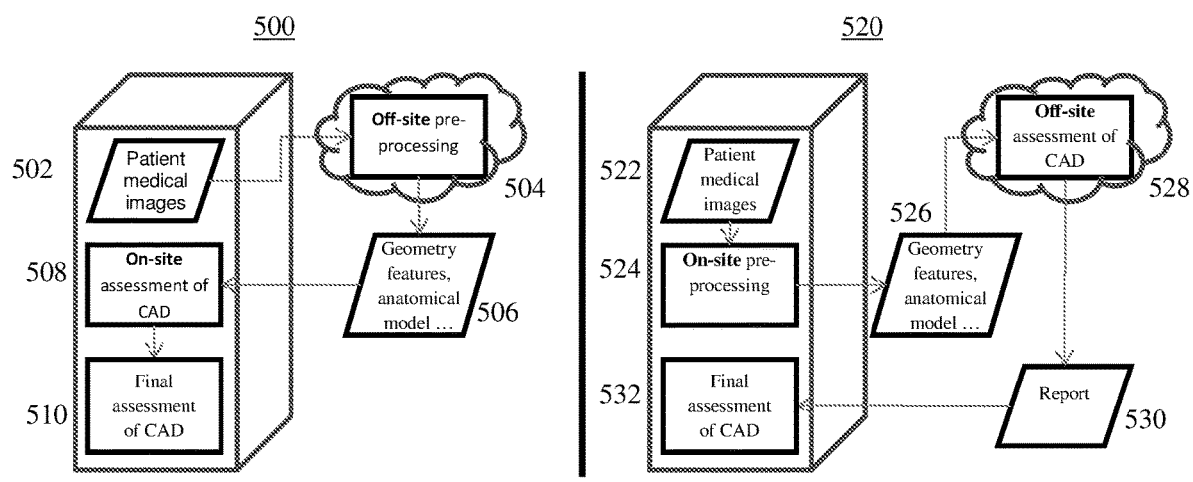
FIG. 5 illustrates exemplary joint on-site and off-site processing strategies in which a pre-processing step is performing using off-site processing and on-site processing.

In another exemplary embodiment, the selection of on-site, off-site, or joint on and off-site processing may be based on the input medical image data of the patient. The modeling technologies implemented on-site or off-site can be better suited for different types of medical image data. In the general framework for patient-specific computational modeling of CAD, medical imaging data are pre-processed to extract geometry features and/or an anatomical model representing the patient's anatomy. In addition, some machine learning-based methods also require the medical imaging data to be pre-processed to extract geometry features and/or an anatomical model. This pre-processing step can be performed using on-site processing or off-site processing dependent on the available tools and the type of medical imaging data used. FIG. 5 illustrates exemplary joint on-site and off-site processing strategies in which a pre-processing step is performing using off-site processing and on-site processing. As shown in FIG. 5, in a first exemplary joint on-site and off-site processing strategy 500, patient medical images 502 are acquired on-site and transmitted to a remote computer system for off-site pre-processing 504. The off-site pre-processing 504 is performed to extract geometry features and/or an anatomical model 506 from the patient medical images 502, and the extracted geometry features and/or anatomical model 506 are returned to the local computer system. On-site assessment of CAD 508 is performed based on the extracted geometry features and/or anatomical model 506, for example using a computational algorithm for CAD assessment or a machine learning based algorithm for CAD assessment, and a final assessment of CAD 510 is performed based on the on-site assessment of CAD 508.

In a second exemplary joint on-site and off-site processing strategy 520, patient medical images 502 are acquired on-site and on-site pre-processing 504 is performed to extract geometry features and/or an anatomical model 506 from the patient medical images. The extracted geometry features and/or anatomical model 506 are transmitted to a remote system for off-site processing in which off-site assessment of CAD 508 is performed. A report 510 including the results of the on-site assessment of CAD 508 is generated and returned to the local computer system, and the final assessment of CAD 512 is performed on-site based on the report 510. This approach can be convenient also in cases in which imaging data or full results of the off site CAD assessment algorithm cannot be sent offline due to size or limited network bandwidth; or due to security or privacy concerns.

In another exemplary embodiment, the selection of on-site, off-site, or joint on and off-site processing may be based on the user. Different tools/algorithms may be best handled by different users. An on-site processing algorithm running on a medical imaging workstation may provide a user interface optimized for use by medical professionals; while tools/algorithms for off-site processing may be tailored for use by non-medical professionals, such as engineers, data scientists, computing scientists, etc.

In another exemplary embodiment, the selection of on-site, off-site, or joint on and off-site processing may be based on the computational resources available. Different processing tools/algorithms have different hardware requirements. In an exemplary implementation, on-site processing can be performed on a medical imaging scanner, or a post-processing workstation. In both cases, the processing unit is not necessarily designed for high performance computing. This can potentially limit the range of processing that can be done on-site, when processing time is also a critical resource to be minimized. Off-site processing can leverage a potentially unlimited freedom in choosing the processing hardware. For instance, off-site processing can be performed on cloud-based computing resources, accessed according to a service-based model (e.g., pay-per-use). This has the advantage of elasticity (the processing task can allocate the required resources on demand, potentially choosing the optimal resources for the task at hand) and availability (both in terms of always having access to computing resources, and having access to high performance hardware without having to maintain/upgrade local computing systems).

In another exemplary embodiment, the selection of on-site, off-site, or joint on and off-site processing may be based on the confidence in the results. For example, in on possible scenario, on-site assessment of FFR may be inconclusive of uncertain due to limitations of the machine-learning based predictor (e.g., the data set being processed has features outside the range considered in the training set). In this case, the off-site processing can include re-training the machine learning algorithm so that the feature values of the new case are within those in the training dataset. Alternatively, a different method can be used in the off-site processing step, such as computational modeling that does not have the same limitation.

The on-site assessment of FFR can be inconclusive or uncertain due to intrinsic uncertainty of the quantity of interest (e.g., computed FFR in the grey zone). In this case, off-site processing can include consulting medical experts (human or databases) to find the best course of action, for instance based on previous clinical cases with similar characteristics.

In another possible scenario, the on-site assessment of FFR provides a first approximation of the quantity of interest (for instance, not all image features can be extracted with confidence). In this case, off-site processing can include further image processing to extract more image features or with more confidence/less uncertainty. Off-site processing can also include evaluating a larger set of features (e.g., plaque burden, but also non-image features such as clinical history of the patient, risk factors for cardiovascular events, etc.) that can be incorporated in the machine learning based predictor to improve the CAD assessment.

In another exemplary embodiment, the selection of on-site, off-site, or joint on and off-site processing may be based on the clinical scenario involving therapy planning. For example, in a possible scenario, the patient is stable, the procedure is not an emergency procedure, and additional information is required to better plan the intervention. In this case, an off-site service could allow device manufacturers to access the patient's imaging information to recommend the optimal device for coronary angioplasty. Off-site processing can also include optimal therapy selection (both medical and surgical/endovascular).

In another exemplary embodiment, the selection of on-site, off-site, or joint on and off-site processing may be based on the use of existing medical imaging data. For example, in a possible scenario, the patient or hospital has medical imaging data from a previous examination (e.g., coronary computed tomography angiography (CCTA)) and the patient is now scheduled for another medical imaging procedure (e.g., Angiography). The already available imaging data may be sent off-site for a preliminary analysis, which may then be useful for the planned procedure. If the same type of data is available at different time points (e.g., CCTA), the data acquired at the current time point may be analyzed on-site and then sent off-site for a comparative analysis with the previous acquisition. This may be used to determine the evolution of the pathology/patient so as to propose the optimal treatment strategy.

An on-site analysis may be performed for the medical imaging data of the patient and then sent off-site for running a different algorithm which may predict the evolution of the pathology in the future (e.g., plaque evolution by employing fluid-solid-growth models). To make the prediction more reliable, periodic measurements may be performed and sent off-site. These periodic measurements may include only basic clinical measurements like heart and blood pressure (e.g., patent may develop hypertension) or medical imaging examinations of the same or different type.

Figure 6:
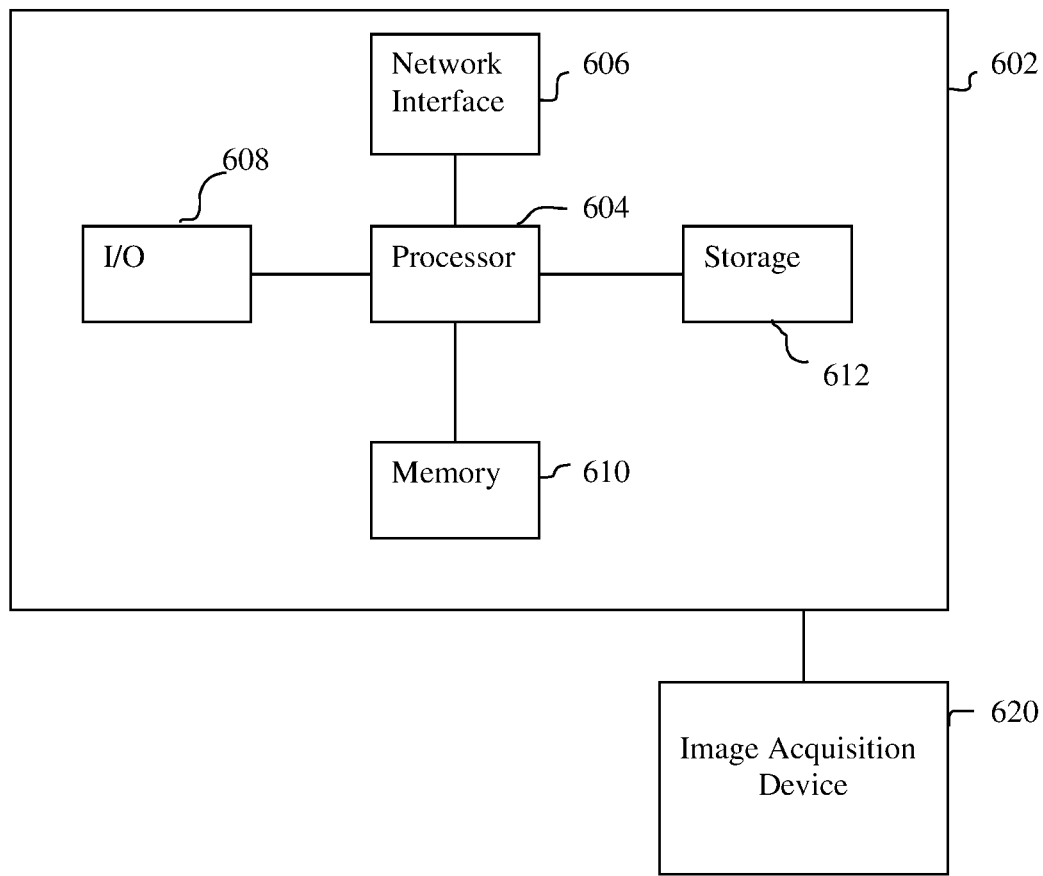
FIG. 6 is a high-level block diagram of a computer capable of implementing the present invention.

The above-described methods may be implemented on one or more computers using well-known computer processors, memory units, storage devices, computer software, and other components. A high-level block diagram of such a computer is illustrated in FIG. 6. Computer 602 contains a processor 604, which controls the overall operation of the computer 602 by executing computer program instructions which define such operation. The computer program instructions may be stored in a storage device 612 (e.g., magnetic disk) and loaded into memory 610 when execution of the computer program instructions is desired. Thus, the steps of the methods of FIGS. 1, 2, 4, and 5 may be defined by the computer program instructions stored in the memory 610 and/or storage 612 and controlled by the processor 604 executing the computer program instructions. An image acquisition device 620, such as a CT scanning device, MR scanning device, Ultrasound device, etc., can be connected to the computer 602 to input image data to the computer 602. It is possible to implement the image acquisition device 620 and the computer 602 as one device. It is also possible that the image acquisition device 620 and the computer 602 communicate wirelessly through a network. In a possible embodiment, the computer 602 may be located remotely with respect to the image acquisition device 620 and the method steps are performed as part of a server or cloud based service. The computer 602 also includes one or more network interfaces 606 for communicating with other devices via a network. The computer 602 also includes other input/output devices 608 that enable user interaction with the computer 602 (e.g., display, keyboard, mouse, speakers, buttons, etc.). Such input/output devices 608 may be used in conjunction with a set of computer programs as an annotation tool to annotate medical image data received from the image acquisition device 620. One skilled in the art will recognize that an implementation of an actual computer could contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for non-invasive assessment of coronary artery disease (CAD) of a patient, comprising:
   receiving medical image data of a patient;
   extracting a clinical indicator of CAD from the medical image data;
   automatically selecting a processing strategy for assessing CAD of the patient using joint on-site and off-site processing using a trained machine learning based intelligent artificial agent based on the clinical indicator of CAD, a purpose for assessing the CAD, and clinical requirements for a current clinical scenario;
   performing non-invasive assessment of the CAD of the patient based on the medical image data of the patient using the joint on-site and off-site processing according to the selected processing strategy;
   determining whether results of the non-invasive assessment of the CAD of the patient using the on-site processing and results of the non-invasive assessment of the CAD of the patient using the off-site processing are consistent; and
   in response to determining that the results of the non-invasive assessment of the CAD of the patient using the on-site processing and the results of the non-invasive assessment of the CAD of the patient using the off-site processing are consistent, determining a final assessment of the CAD of the patient by combining the results of the non-invasive assessment of the CAD of the patient using the on-site processing and the results of the non-invasive assessment of the CAD of the patient using the off-site processing.

2. The method of claim 1, wherein automatically selecting a processing strategy for assessing CAD of the patient using joint on-site and off-site processing using a trained machine learning based intelligent artificial agent based on the clinical indicator of CAD, a purpose for assessing the CAD, and clinical requirements for a current clinical scenario comprises:
   automatically selecting the processing strategy for assessing the CAD of the patient using the joint on-site and off-site processing based on the clinical requirements including one or more of time requirements, fidelity requirements, computing resources currently available on-site, or a type of the medical image data.

3. The method of claim 1, wherein:
   extracting a clinical indicator of CAD from the medical image data comprises:
      performing calcium scoring in the medical image data of the patient using a trained machine learning based classifier; and
   automatically selecting a processing strategy for assessing CAD of the patient using joint on-site and off-site processing using a trained machine learning based intelligent artificial agent based on the clinical indicator of CAD, a purpose for assessing the CAD, and clinical requirements for a current clinical scenario comprises:
      automatically selecting the processing strategy for assessing CAD of the patient using the joint on-site and off-site processing based on the calcium scoring in the medical image data of the patient.

4. The method of claim 1, wherein automatically selecting a processing strategy for assessing CAD of the patient using joint on-site and off-site processing using a trained machine learning based intelligent artificial agent based on the clinical indicator of CAD, a purpose for assessing the CAD, and clinical requirements for a current clinical scenario comprises:
   automatically selecting the processing strategy using a trained deep neural network (DNN) based on the clinical indicator of CAD input to the trained DNN, wherein the trained DNN is trained using deep reinforcement learning based on a database of patient-specific medical image data for various patients and corresponding outcomes or clinical histories of the various patients.

5. The method of claim 4, wherein the clinical indicator is a calcium scoring of the medical image data of the patient.

6. The method of claim 1, wherein the on-site processing utilizes a machine learning based CAD assessment algorithm and the off-site processing utilizes a CAD assessment algorithm based on computational modeling.

7. The method of claim 1, wherein the on-site processing utilizes a first computational CAD assessment algorithm and the off-site processing utilizes a second computational CAD assessment algorithm with a higher fidelity computational model of coronary artery blood flow than the first computational CAD assessment algorithm.

8. The method of claim 1, wherein performing non-invasive assessment of the CAD of the patient based on the medical image data of the patient using the joint on-site and off-site processing according to the selected processing strategy comprises:
   performing one or more operations of a CAD assessment algorithm using the on-site processing and one or more operations of the CAD assessment algorithm using the off-site processing.

9. The method of claim 1, further comprising:
   automatically determining whether additional processing is necessary for assessing the CAD of the patient; and
   in response to a determination that additional processing is necessary for assessing the CAD of the patient, automatically selecting an updated processing strategy for assessing the CAD of the patient using one of on-site processing, off-site processing, or the joint on-site and off-site processing based on the clinical requirements for the current clinical scenario and the final assessment of CAD performed using the previous processing strategy.

10. An apparatus for non-invasive assessment of coronary artery disease (CAD) of a patient, comprising:
   means for receiving medical image data of a patient;
   means for extracting a clinical indicator of CAD from the medical image data;
   means for automatically selecting a processing strategy for assessing CAD of the patient using joint on-site and off-site processing using a trained machine learning based intelligent artificial agent based on the clinical indicator of CAD, a purpose for assessing the CAD, and clinical requirements for a current clinical scenario;
   means for performing non-invasive assessment of the CAD of the patient based on the medical image data of the patient using the joint on-site and off-site processing according to the selected processing strategy;

means for determining whether results of the non-invasive assessment of the CAD of the patient using the on-site processing and results of the non-invasive assessment of the CAD of the patient using the off-site processing are consistent; and means for determining a final assessment of the CAD of the patient by combining the results of the non-invasive assessment of the CAD of the patient using the on-site processing and the results of the non-invasive assessment of the CAD of the patient using the off-site processing in response to determining that the results of the non-invasive assessment of the CAD of the patient using the on-site processing and the results of the non-invasive assessment of the CAD of the patient using the off-site processing are consistent.

11. The apparatus of claim 10, wherein the means for automatically selecting a processing strategy for assessing CAD of the patient using joint on-site and off-site processing using a trained machine learning based intelligent artificial agent based on the clinical indicator of CAD, a purpose for assessing the CAD, and clinical requirements for a current clinical scenario comprises:
means for automatically selecting the processing strategy for assessing the CAD of the patient using the joint on-site and off-site processing based on the clinical requirements including one or more of time requirements, fidelity requirements, computing resources currently available on-site, or a type of the medical image data.

12. The apparatus of claim 10, further comprising:
means for automatically determining whether additional processing is necessary for assessing the CAD of the patient; and
means for automatically selecting an updated processing strategy for assessing the CAD of the patient using one of on-site processing, off-site processing, or the joint on-site and off-site processing based on the clinical requirements for the current clinical scenario and the final assessment of CAD performed using the previous processing strategy in response to a determination that additional processing is necessary for assessing the CAD of the patient.

13. A non-transitory computer readable medium storing computer program instructions for non-invasive assessment of coronary artery disease (CAD) of a patient, the computer program instructions when executed by a processor cause the processor to perform operations comprising:
receiving medical image data of a patient;
extracting a clinical indicator of CAD from the medical image data;
automatically selecting a processing strategy for assessing CAD of the patient using joint on-site and off-site processing using a trained machine learning based intelligent artificial agent based on the clinical indicator of CAD, a purpose for assessing the CAD, and clinical requirements for a current clinical scenario;
performing non-invasive assessment of the CAD of the patient based on the medical image data of the patient using the joint on-site and off-site processing according to the selected processing strategy;
determining whether results of the non-invasive assessment of the CAD of the patient using the on-site processing and results of the non-invasive assessment of the CAD of the patient using the off-site processing are consistent; and
in response to determining that the results of the non-invasive assessment of the CAD of the patient using the on-site processing and the results of the non-invasive assessment of the CAD of the patient using the off-site processing are consistent, determining a final assessment of the CAD of the patient by combining the results of the non-invasive assessment of the CAD of the patient using the on-site processing and the results of the non-invasive assessment of the CAD of the patient using the off-site processing.

14. The non-transitory computer readable medium of claim 13, wherein automatically selecting a processing strategy for assessing CAD of the patient using joint on-site and off-site processing using a trained machine learning based intelligent artificial agent based on the clinical indicator of CAD, a purpose for assessing the CAD, and clinical requirements for a current clinical scenario comprises:
automatically selecting the processing strategy for assessing the CAD of the patient using the joint on-site and off-site processing based on the clinical requirements including one or more of time requirements, fidelity requirements, computing resources currently available on-site, or a type of the medical image data.

15. The non-transitory computer readable medium of claim 13, wherein:
extracting a clinical indicator of CAD from the medical image data comprises:
performing calcium scoring in the medical image data of the patient using a trained machine learning based classifier; and
automatically selecting a processing strategy for assessing CAD of the patient using joint on-site and off-site processing using a trained machine learning based intelligent artificial agent based on the clinical indicator of CAD, a purpose for assessing the CAD, and clinical requirements for a current clinical scenario comprises:
automatically selecting the processing strategy for assessing CAD of the patient using the joint on-site and off-site processing based on the calcium scoring in the medical image data of the patient.

16. The non-transitory computer readable medium of claim 13, wherein performing non-invasive assessment of the CAD of the patient based on the medical image data of the patient using the joint on-site and off-site processing according to the selected processing strategy comprises:
performing one or more operations of a CAD assessment algorithm using the on-site processing and one or more operations of the CAD assessment algorithm using the off-site processing.

17. The non-transitory computer readable medium of claim 13, wherein the operations further comprise:
automatically determining whether additional processing is necessary for assessing the CAD of the patient; and
in response to a determination that additional processing is necessary for assessing the CAD of the patient, automatically selecting an updated processing strategy for assessing the CAD of the patient using one of on-site processing, off-site processing, or the joint on-site and off-site processing based on the clinical requirements for the current clinical scenario and the final assessment of CAD performed using the previous processing strategy.

* * * * *